United States Patent [19]

Edwards

[11] Patent Number: Plant 6,656

[45] Date of Patent: Mar. 7, 1989

[54] *JUNIPERUS SABINA* CV. MONARD

[75] Inventor: Charles W. Edwards, Azusa, Calif.

[73] Assignee: Monrovia Nursery Company, Azusa, Calif.

[21] Appl. No.: 93,693

[22] Filed: Sep. 4, 1987

[51] Int. Cl.[4] ..... A01H 5/00

[52] U.S. Cl. ..... Plt./50

[58] Field of Search ..... Plt./50

*Primary Examiner*—Robert E. Bagwill

[57] ABSTRACT

A new and distinct selection of *Juniperus sabina* L. shrub (popularly known savin juniper) which shall be referred to hereinafter as *Juniperus sabina* cultivar Monard. *Juniperus sabina* cultivar Monard differs from its parent, *Juniperus sabina* cv. Broadmoor by a unique combination of a flatter more symmetrical branching habit, a softer foliage texture, a more green color and higher rooting percentages.

1 Drawing Sheet

DISCOVERY

This invention relates to a new and distinct selection of *Juniperus sabina,* a member of the Cupressaceae or Cypress family. *Juniperus sabina* cultivar Monard was selected by me from a large group of containerized *Juniperus sabina* cv. Broadmoor in Spring of 1981 within the boundaries of Monrovia Nursery Company, 18331 E. Foothill Blvd., Azusa, Calif.

REPRODUCTION

My new selection has been strictly asexually reproduced by cuttings at Monrovia Nursery Company. The unique characteristics that set this selection apart from the parent plant and make it a new and distinct selection would be lost in sexual reproduction. Therefore, propagation is restricted to asexual reproduction and sexual reproduction is prohibited.

BRIEF DESCRIPTION OF THE DRAWINGS

The accompanying illustrations show a typical specimen of the plant according to this invention and are depicted in color as nearly true as possible.

FIG. 1 shows a comparison of my selection on the right and 'Broadmoor' prior art on the left. My selection exhibits a flatter, overlapping more symmetrical branching habit and a more green color of foliage. The prior art on the left has a slight blue tint due to the more juvenile foliage which is particularly exhibited in the lower front area of the plant.

FIG. 2 exhibits a close up of my selection depicting the more adult foliage which gives an overall softer appearance in comparison to the more needle like foliage of the prior art. (See FIG. 1).

DESCRIPTION

Below is a detailed description of the new *Juniperus sabina* cv. Monard, the color terminology is from the British Horticultural Colour Charts.

Overall size and habit: Evergreen conifer, a prostrate shrub, ground hugging habit, eventual size predicted to be 6 to 7 inches in height and 4 feet in spread. In comparison, Broadmoor, the parent is 15–20 inches in height and 6 feet in spread.

Foliage:

*Juvenile.*—Size: ⅛ to 3/16 inch long; 1/16 inch wide. Arrangement: Slightly spreading at a 45 degree angle. Glaucous bloom: Present on new foliage. Color: With glaucous bloom Sky Grey 449/2. Outer leaf surface: Leek Green 000858. Shape: Acicular.

*Mature.*—Size: 1/16–⅛ inch long; 1/16 inch wide at base. Arrangement: Adhering closely to the stems. Glaucous bloom: Covering foliage, not present on outer tip of leaf. Color: Leaf surface — Spinach Green 0960/2. Shape: Subulate.

Fruit: No fruit observed and not significant.

Foliage texture comparison: Appears soft adult foliage about 90% sharp juvenile foliage about 10%; 'Broadmoor' adult foliage 10% sharp juvenile foliage about 90%.

Overall color comparison: More green, 'Broadmoor' due to juvenile foliage with glaucous color appears more blue green.

Comparison of rooting percentages: Approximately 65–75%, 'Broadmoor' 60 to 70%.

I claim:

1. A new and distinct selection of *Juniperus sabina* as substantially shown and described herein, that is characterized particularly as a novelty by the unique combination of a flatter more symmetrical branching habit, a softer foliage texture, a more green color and higher rooting percentages.

* * * * *

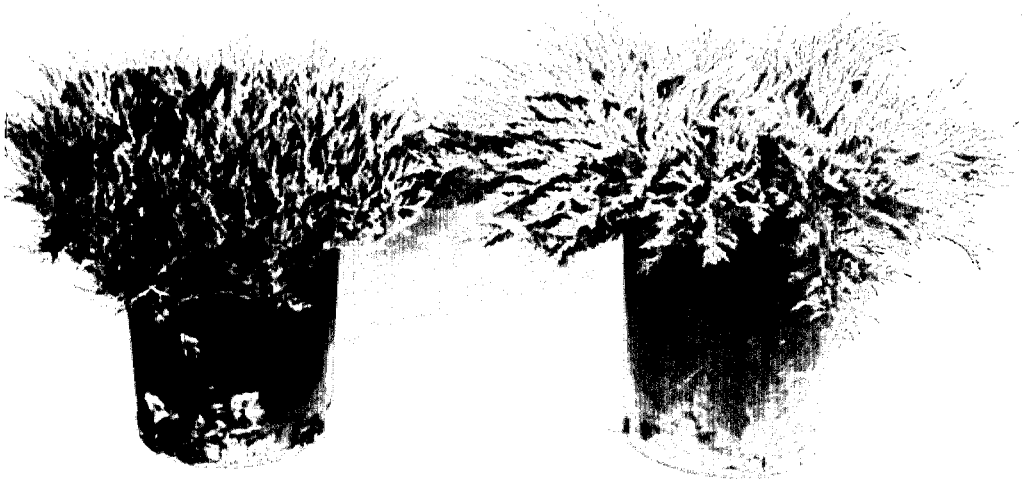
FIG.1 PRIOR ART & SELECTION
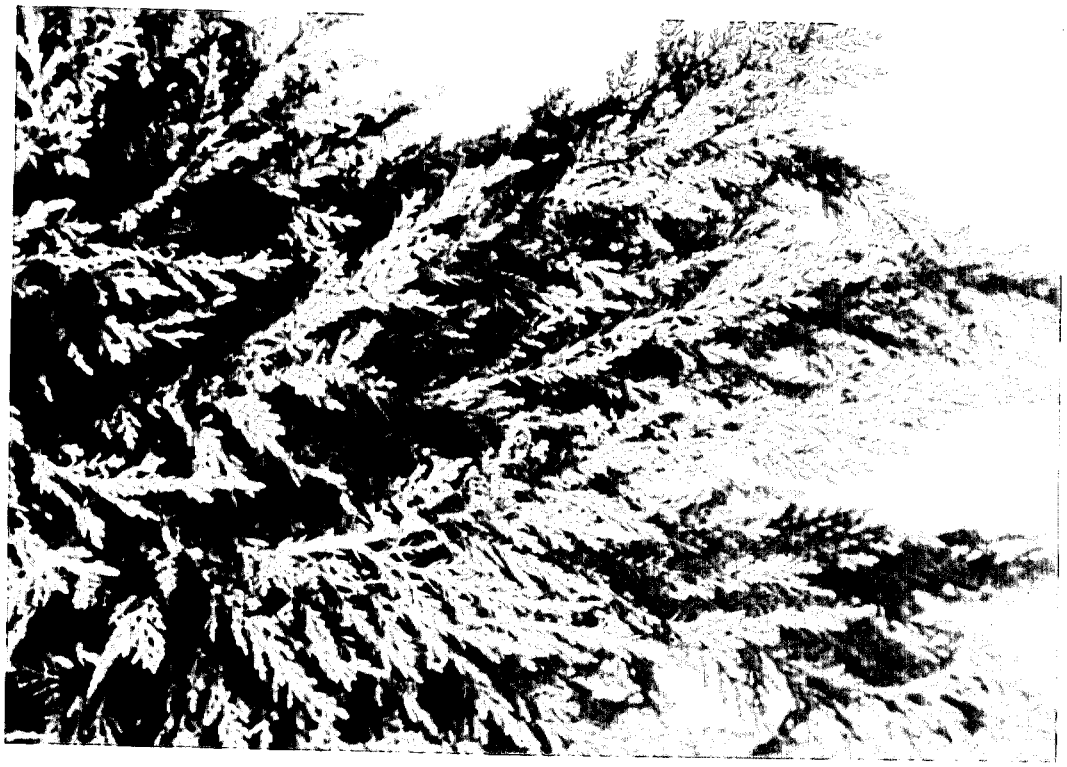
FIG.2. SELECTION